(12) United States Patent
Nazarifar et al.

(10) Patent No.: US 8,430,840 B2
(45) Date of Patent: Apr. 30, 2013

(54) INTRAOCULAR PRESSURE CONTROL

(75) Inventors: Nader Nazarifar, Laguna Niguel, CA (US); Frederick Reed, Cypress, CA (US); John C. Huculak, Mission Viejo, CA (US); Roger Thomas, Tustin, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/267,376

(22) Filed: Oct. 6, 2011

(65) Prior Publication Data

US 2012/0029423 A1 Feb. 2, 2012

Related U.S. Application Data

(60) Continuation of application No. 11/969,091, filed on Jan. 3, 2008, now abandoned, which is a division of application No. 11/237,503, filed on Sep. 28, 2005, now Pat. No. 7,326,183.

(51) Int. Cl.
*A61M 1/00* (2006.01)
*A61M 31/00* (2006.01)
*A61M 5/00* (2006.01)

(52) U.S. Cl.
USPC ............... 604/30; 604/505; 604/246; 604/65

(58) Field of Classification Search .............. 604/30–35, 604/66, 67, 80, 82, 85, 118, 131, 132, 147, 604/151, 153, 245, 246, 249
See application file for complete search history.

(56) References Cited

U.S. PATENT DOCUMENTS

| | | | |
|---|---|---|---|
| 4,197,196 A | 4/1980 | Pinkerton | |
| 4,475,904 A | 10/1984 | Wang | |
| 4,637,817 A * | 1/1987 | Archibald et al. | 604/81 |
| 4,713,051 A | 12/1987 | Steppe et al. | |
| 4,750,643 A | 6/1988 | Wortrich | |
| 4,758,238 A | 7/1988 | Sundblom et al. | |
| 4,813,927 A | 3/1989 | Morris et al. | |
| 4,832,685 A | 5/1989 | Haines | |
| 4,846,800 A | 7/1989 | Ouriel et al. | |
| 4,865,584 A | 9/1989 | Epstein et al. | |
| 4,900,301 A | 2/1990 | Morris et al. | |
| 4,909,780 A | 3/1990 | Ouriel et al. | |
| 4,935,005 A | 6/1990 | Haines | |
| 4,963,131 A | 10/1990 | Wortrich | |
| 5,006,050 A * | 4/1991 | Cooke et al. | 417/478 |
| 5,032,111 A | 7/1991 | Morris et al. | |

(Continued)

FOREIGN PATENT DOCUMENTS

| | | |
|---|---|---|
| CA | 1068572 | 12/1979 |
| CA | 1068574 | 12/1979 |

(Continued)

OTHER PUBLICATIONS

Oda H; Bibliographic data: JP 8010281 (A); Jan. 16, 1996; abstract only; espacenet.com; 1 page.

(Continued)

*Primary Examiner* — Kevin C. Sirmons
*Assistant Examiner* — William Carpenter
(74) *Attorney, Agent, or Firm* — W. David Lee

(57) ABSTRACT

An improved method of controlling intraocular pressure with a microsurgical system using measured flow rate.

1 Claim, 2 Drawing Sheets

U.S. PATENT DOCUMENTS

| | | | |
|---|---|---|---|
| 5,041,096 A | 8/1991 | Beuchat et al. | |
| 5,047,009 A | 9/1991 | Morris et al. | |
| 5,098,037 A | 3/1992 | Leffel et al. | |
| 5,106,366 A | 4/1992 | Steppe | |
| 5,163,900 A | 11/1992 | Wortrich | |
| 5,267,956 A | 12/1993 | Beuchat | |
| 5,282,787 A | 2/1994 | Wortrich | |
| D352,106 S | 11/1994 | Fanney et al. | |
| 5,364,342 A | 11/1994 | Beuchat et al. | |
| 5,499,969 A | 3/1996 | Beuchat et al. | |
| 5,563,584 A | 10/1996 | Rader et al. | |
| D375,553 S | 11/1996 | Creed et al. | |
| 5,582,601 A | 12/1996 | Wortrich et al. | |
| 5,588,815 A | 12/1996 | Zaleski, II | |
| 5,620,312 A | 4/1997 | Hyman et al. | |
| 5,630,798 A | 5/1997 | Beiser et al. | |
| D380,550 S | 7/1997 | Dennewill et al. | |
| 5,643,203 A | 7/1997 | Beiser et al. | |
| 5,647,853 A | 7/1997 | Feldmann et al. | |
| 5,676,530 A | 10/1997 | Nazarifar | |
| 5,676,650 A * | 10/1997 | Grieshaber et al. | 604/28 |
| 5,700,240 A | 12/1997 | Barwick, Jr. et al. | |
| 5,747,824 A | 5/1998 | Jung et al. | |
| 5,776,104 A | 7/1998 | Guignard et al. | |
| 5,800,396 A | 9/1998 | Fanney et al. | |
| 5,810,765 A | 9/1998 | Oda | |
| 5,830,176 A | 11/1998 | Mackool | |
| 5,865,764 A | 2/1999 | Moorhead | |
| 5,865,794 A * | 2/1999 | Castro | 604/508 |
| 5,897,524 A | 4/1999 | Wortrich et al. | |
| 5,899,674 A | 5/1999 | Jung et al. | |
| 6,059,544 A | 5/2000 | Jung et al. | |
| 6,261,283 B1 | 7/2001 | Morgan et al. | |
| 6,293,926 B1 | 9/2001 | Sorensen et al. | |
| 6,485,454 B1 | 11/2002 | Yueh | |
| 6,491,661 B1 | 12/2002 | Boukhny et al. | |
| 6,561,999 B1 | 5/2003 | Nazarifar et al. | |
| 6,572,349 B2 | 6/2003 | Sorensen et al. | |
| 6,579,255 B2 | 6/2003 | Kadziauskas et al. | |
| 6,632,214 B2 | 10/2003 | Morgan et al. | |
| 6,740,074 B2 | 5/2004 | Morgan et al. | |
| 6,824,525 B2 | 11/2004 | Nazarifar et al. | |
| 6,902,542 B2 | 6/2005 | Gordon | |
| 6,962,488 B2 | 11/2005 | Davis et al. | |
| 2001/0023345 A1 | 9/2001 | Wolff et al. | |
| 2002/0019607 A1 | 2/2002 | Bui | |
| 2002/0033370 A1 | 3/2002 | Bainbridge et al. | |
| 2003/0050619 A1 | 3/2003 | Mooijman et al. | |
| 2003/0108429 A1 | 6/2003 | Angelini et al. | |
| 2003/0196693 A1 * | 10/2003 | Schwindt | 137/2 |
| 2003/0225363 A1 | 12/2003 | Gordon et al. | |
| 2004/0253129 A1 | 12/2004 | Sorensen et al. | |
| 2005/0065462 A1 | 3/2005 | Nazarifar et al. | |

FOREIGN PATENT DOCUMENTS

| | | |
|---|---|---|
| DE | 19852574 A1 | 5/2000 |
| EP | 0776670 B1 | 9/2001 |
| EP | 1356835 A1 | 10/2003 |
| EP | 1612532 A1 | 1/2006 |
| WO | 98/25515 A1 | 6/1998 |
| WO | 03047652 A1 | 6/2003 |
| WO | 03047653 A1 | 6/2003 |
| WO | 03047654 A1 | 6/2003 |

OTHER PUBLICATIONS

Hanamura Y et al.; Bibliographic data: JP 2107245 (A); Apr. 19, 1990; abstract only; espacenet.com; 1 page.

* cited by examiner

INTRAOCULAR PRESSURE CONTROL

This application is a continuation of U.S. application Ser. No. 11/969,091 filed on Jan. 3, 2008 now abandoned which is a divisional of U.S. application Ser. No. 11/237,503 filed on Sep. 28, 2005 now U.S. Pat. No. 7,326,183.

FIELD OF THE INVENTION

The present invention generally pertains to microsurgical systems and more particularly to controlling intraocular pressure in ophthalmic surgery.

DESCRIPTION OF THE RELATED ART

During small incision surgery, and particularly during ophthalmic surgery, small probes are inserted into the operative site to cut, remove, or otherwise manipulate tissue. During these surgical procedures, fluid is typically infused into the eye, and the infusion fluid and tissue are aspirated from the surgical site.

Maintaining an optimum intraocular pressure during ophthalmic surgery is currently problematic. When no aspiration is occurring, the pressure in the eye becomes the pressure of the fluid being infused into the eye. This pressure is typically referred to as the "dead head pressure". However, when aspiration is applied, the intraocular pressure drops dramatically from the dead head pressure due to all the pressure losses in the aspiration circuit associated with aspiration flow. Therefore, ophthalmic surgeons currently tolerate higher than desired dead head pressures to compensate for occasions when aspiration would otherwise lower the intraocular pressure to soft-eye conditions. Clinically, such over-pressurizing of the eye is not ideal.

Accordingly, a need continues to exist for an improved method of controlling intraocular pressure during ophthalmic surgery.

SUMMARY OF THE INVENTION

In one aspect, the present invention is a microsurgical system for controlling intraocular pressure including a surgical cassette having an infusion chamber for containing irrigating fluid; a pressurized gas source; a proportional valve; a gas line fluidly coupling the pressurized gas source, the proportional valve, and the infusion chamber in the surgical cassette; a surgical device for providing the irrigating fluid to an eye; a fluid line fluidly coupling the infusion chamber in the surgical cassette and the surgical device; a flow sensor operatively coupled to the fluid line between the infusion chamber in the surgical cassette and the surgical device; a user input; and a computer electrically coupled to the proportional valve, the flow sensor, and the user input. When a user selects a desired intraocular pressure via the input, the computer sends a first signal to the proportional valve to provide an appropriate level of pressurized gas to the infusion chamber in the surgical cassette so as to provide the irrigating fluid from the infusion chamber to the surgical device and the eye via the fluid line, the flow sensor measures a flow rate of the irrigating fluid in the fluid line and provides a second signal to the computer, the computer calculates a predicted intraocular pressure using the second signal and empirically determined impedance information for the microsurgical system, and the computer sends a third signal to the proportional valve to maintain the predicted intraocular pressure proximate the desired intraocular pressure.

BRIEF DESCRIPTION OF THE DRAWINGS

For a more complete understanding of the present invention, and for further objects and advantages thereof, reference is made to the following description taken in conjunction with the accompanying drawings, in which.

DETAILED DESCRIPTION OF THE PREFERRED EMBODIMENTS

Figure 1:
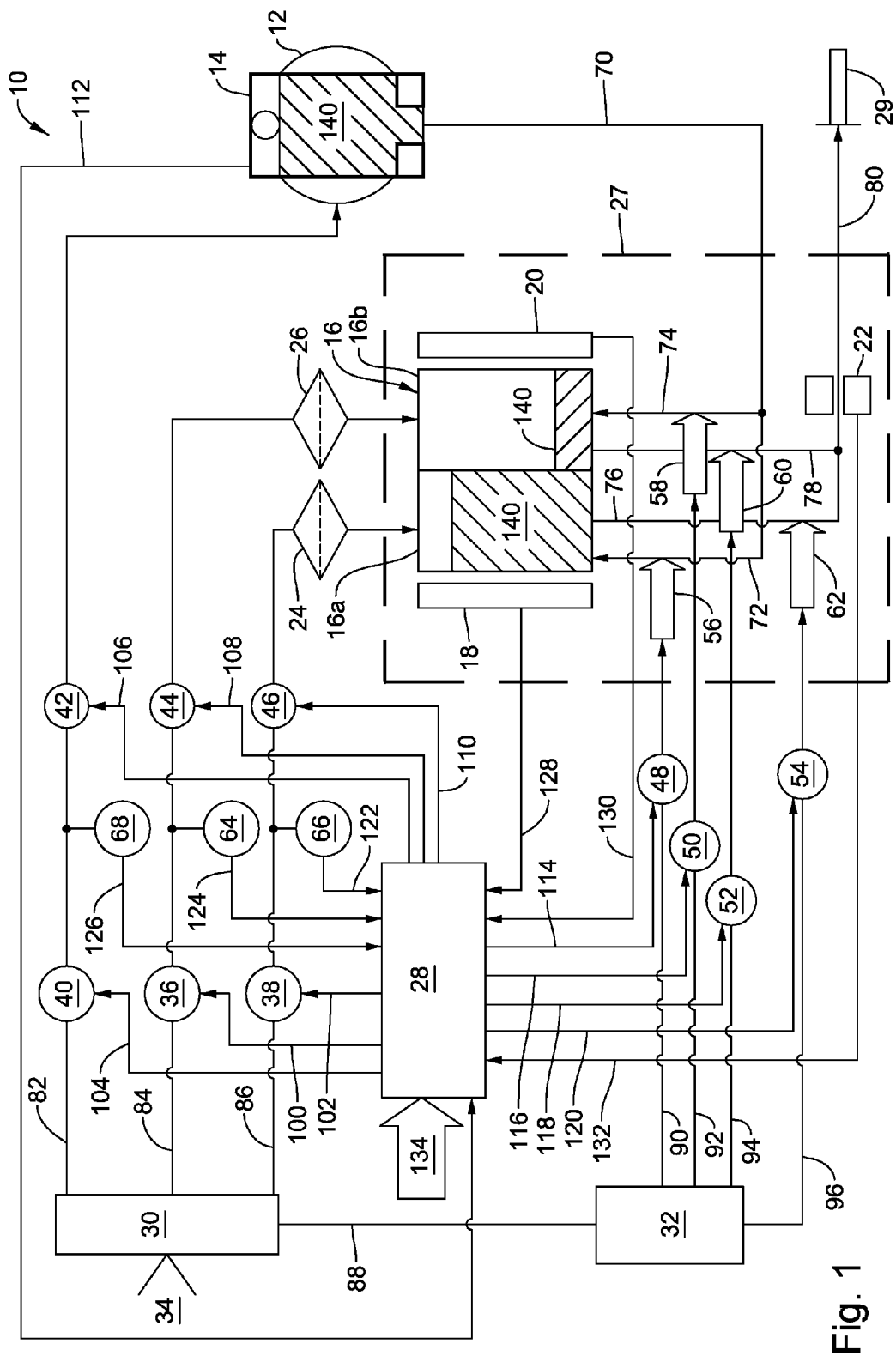
FIG. 1 is a schematic diagram illustrating infusion control in an ophthalmic microsurgical system.
Figure 2:
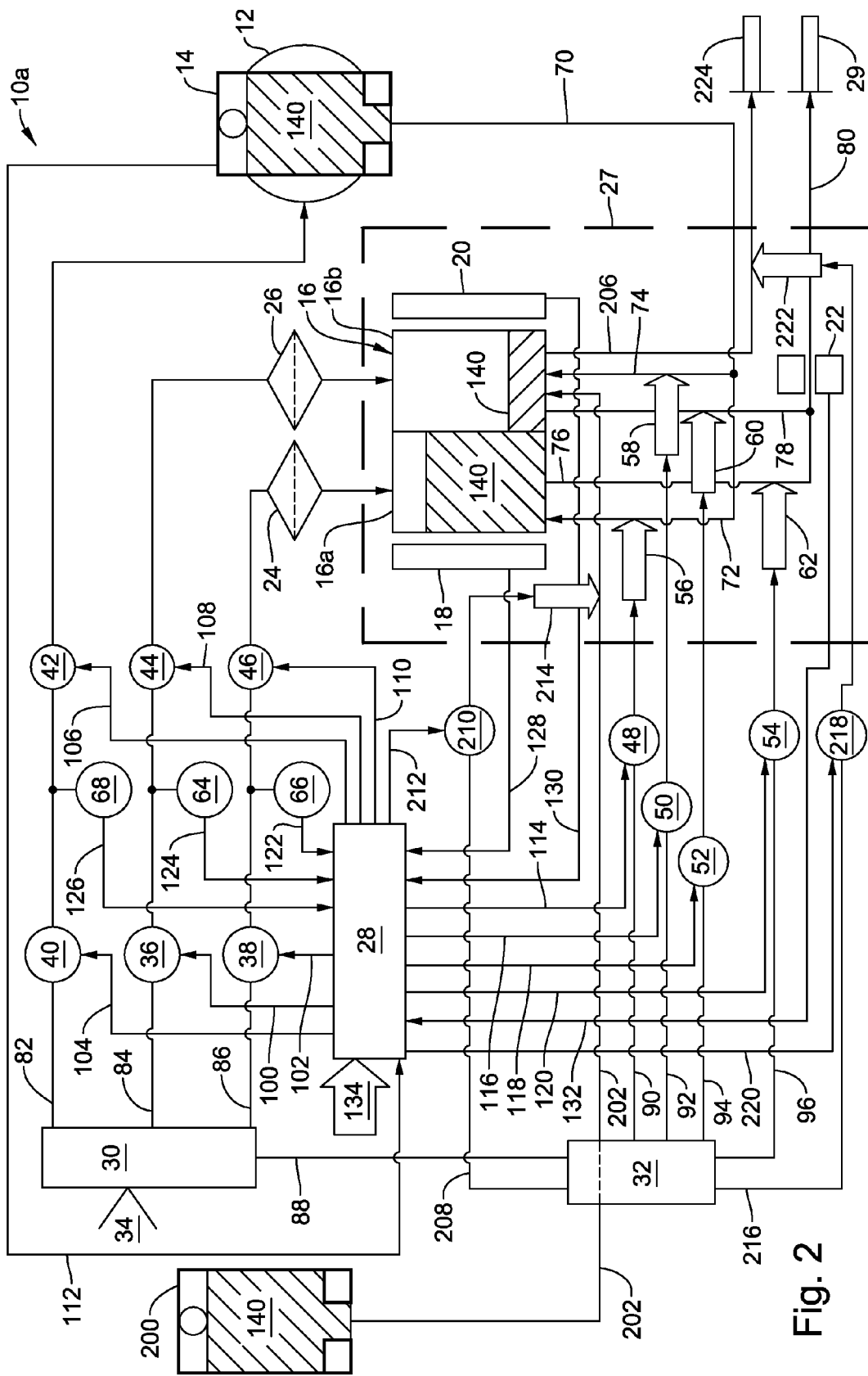
FIG. 2 is a schematic diagram illustrating infusion control and irrigation control in an ophthalmic microsurgical system.

The preferred embodiments of the present invention and their advantages are best understood by referring to FIGS. 1-2 of the drawings, like numerals being used for like and corresponding parts of the various drawings. As shown in FIG. 1, ophthalmic microsurgical system 10 includes a pressure cuff 12; an infusion source 14; a dual infusion chamber 16 having a chamber 16a and a chamber 16b; fluid level sensors 18 and 20; a flow sensor 22; filters 24 and 26; a surgical device 29; a computer or microprocessor 28; gas manifolds 30 and 32; a pressurized gas source 34; proportional solenoid valves 36, 38, and 40; "on/off" solenoid valves 42, 44, 46, 48, 50, 52, 54; actuators 56, 58, 60, and 62; and pressure transducers 64, 66, and 68. Dual infusion chamber 16; fluid level sensors 18 and 20; portions of infusion fluid lines 70, 72, 74, 76, 78, and 80; and portions of gas lines 84 and 86 are preferably disposed in a surgical cassette 27. Infusion source 14; dual infusion chamber 16; flow sensor 22; filters 24 and 26; and surgical device 29 are fluidly coupled via infusion fluid lines 70-80. Infusion source 14, dual infusion chamber 16, gas manifolds 30 and 32; pressurized gas source 34; and actuators 56, 58, 60, and 62 are fluidly coupled via gas lines 82, 84, 86, 88, 90, 92, 94, and 96. Infusion source 14; fluid level sensors 18-20; flow sensor 22; microprocessor 28; proportional solenoid valves 36-40; on/off solenoid valves 42-54; actuators 56-62; and pressure transducers 64-68 are electrically coupled via interfaces 100, 102, 104, 106, 108, 110, 112, 114, 116, 118, 120, 122, 124, 126, 128, 130, and 132.

Infusion source 14 is preferably a flexible infusion source. Fluid level sensors 18 and 20 may be any suitable device for measuring the level of fluid in infusion chambers 16a and 16b, respectively. Fluid level sensors 18 and 20 are preferably capable of measuring the level of fluid in infusion chambers 16a and 16b in a continuous manner. Flow sensor 22 may be any suitable device for measuring the flow rate of fluid within fluid line 80. Flow sensor 22 is preferably a non-invasive flow sensor. Filters 24 and 26 are hydrophobic micro-bacterial filters. A preferred filter is the Versapor® membrane filter (0.8 micron) available from Pall Corporation of East Hills, N.Y. Microprocessor 28 is capable of implementing feedback control, and preferably PID control. Surgical device 29 may be any suitable device for providing surgical irrigating fluid to the eye but is preferably an infusion cannula, an irrigation handpiece, or and irrigation/aspiration handpiece.

In operation, fluid lines 70, 72, and 74; chambers 16a and 16b; fluid lines 76, 78, and 80; and surgical device 29 are all primed with a surgical irrigating fluid 140 by pressurizing infusion source 14. Surgical irrigating fluid 140 may be any surgical irrigating fluid suitable for ophthalmic use, such as, by way of example, BSS PLUS® intraocular irrigating solution available from Alcon Laboratories, Inc.

The pressurizing of infusion source 14 is preferably performed by pressure cuff 12. More specifically, microprocessor 28 sends a control signal to open solenoid valve 42 via interface 106 and to close solenoid valves 44 and 46 via interfaces 108 and 110, respectively. Microprocessor 28 also sends a control signal to open proportional solenoid valve 40 via interface 104 so that manifold 30 supplies the appropriate amount of pressurized air to actuate pressure cuff 12. Pressure transducer 68 senses the pressure within gas line 82 and provides a corresponding signal to microprocessor 28 via interface 126. Solenoid valves 48-54 are initially open so that manifold 32 provides pressurized air to actuate actuators 56-62 to close fluid lines 72-78. Microprocessor 28 sends control signals to close solenoid valves 48-54 via interfaces 114-120. The closing of solenoid valves 48-54 actuates actuators 56-62 to open fluid lines 72-78. After all chambers and fluid lines are primed, microprocessor 28 closes actuators 56-62 and thus fluid lines 72-78. Alternatively, the pressuring of infusion source 14 may be performed solely via gravity.

After priming, a user then provides a desired intraocular pressure to microprocessor 28 via an input 134. Input 134 may be any suitable input device but is preferably a touch screen display or physical knob. Chamber 16b is preferably the initial active infusion chamber. Microprocessor 28 sends appropriate control signals to open solenoid valve 44 and to open proportional solenoid valve 36 (via interface 100) to provide an appropriate level of pressurized air to chamber 16b. Pressure transducer 64 senses the pressure within gas line 84 and provides a corresponding signal to microprocessor 28 via interface 124. Microprocessor 28 also sends an appropriate control signal to open actuator 60 and thus fluid line 78. Chamber 16b supplies pressurized fluid 140 to the eye via fluid lines 78 and 80 and surgical device 29. Flow sensor 22 measures the flow rate of fluid 140 and provides a corresponding signal to microprocessor 28 via interface 132. Microprocessor 28 calculates a predicted intraocular pressure using the signal from flow sensor 22 and empirically determined impedance information of microsurgical system 10. Microprocessor 28 then sends an appropriate feedback control signal to proportional solenoid valve 36 to maintain the predicted intraocular pressure at or near the desired intraocular pressure during all portions of the surgery.

Fluid level sensor 20 continuously monitors the decrease in the level of fluid 140 in chamber 16b during surgery and provides a corresponding signal to microprocessor 28 via interface 130. Microprocessor 28 performs adjustments to the air pressure provided to chamber 16b to accommodate for the difference in fluid head height as the level of fluid 140 decreases. When the level of fluid 140 in chamber 16b reaches a bottom limit level, microprocessor 28 closes solenoid valve 44 and actuator 60 and opens solenoid valve 46 and actuators 58 and 62. Chamber 16a is now the active infusion chamber. Microprocessor 28 sends an appropriate control signal to proportional solenoid valve 38 via interface 102 to provide an appropriate level of pressurized air to chamber 16a. Pressure transducer 66 senses the pressure within gas line 86 and provides a corresponding signal to microprocessor 28 via interface 122. Chamber 16a supplies pressurized fluid 140 to the eye via fluid lines 76 and 80 and surgical device 29. Flow sensor 22 measures the flow rate of fluid 140 and provides a corresponding signal to microprocessor 28 via interface 132. Microprocessor 28 calculates the predicted intraocular pressure as described above and the sends an appropriate feedback signal to proportional solenoid valve 38 to maintain the predicted intraocular pressure at or near the desired intraocular pressure during all portions of the surgery. Microprocessor 28 closes actuator 58 and fluid line 74 once chamber 16b is refilled with fluid 140.

Fluid level sensor 18 continuously monitors the decrease in the level of fluid 140 in chamber 16a during surgery and provides a corresponding signal to microprocessor 28 via interface 128. Microprocessor 28 performs adjustments to the air pressure provided to chamber 16a to accommodate for the difference in fluid head height as the level of fluid 140 decreases. When the level of fluid 140 in chamber 16a reaches a bottom limit level, microprocessor 28 switches chamber 16b to active infusion, makes chamber 16a inactive, and refills chamber 16a with fluid 140 via fluid line 72. This cycling between chambers 16b and 16a continues throughout the surgery.

Infusion source 14 is preferably monitored via a fluid level sensor (not shown) capable of providing a signal to microprocessor 28 via interface 112 when source 14 reaches a near empty limit. Chambers 16a and 16b also preferably each have a volume that enable infusion source 14 to be exchanged, when near empty, without interrupting the surgical procedure. More specifically, chambers 16a and 16b preferably each have a volume of about 30 cc. Such volume allows about two minutes for a near empty infusion source 14 to be exchanged during conditions of maximum flow (e.g. core vitrectomy). In addition, once infusion source 14 is exchanged, all air bubbles within fluid lines 70, 72, and 74 will be automatically "scrubbed out" as the inactive chamber 16a or 16b refills, without the need for re-priming.

In the case of failure of either of chambers 16a or 16b, microprocessor 28 can preferably continue surgery with only one active chamber. In the case of failure of both chambers 16a and 16b, microprocessor 28 can preferably continue surgery using only infusion source 14.

FIG. 2 shows a modified ophthalmic microsurgical system 10a. Microsurgical system 10a is similar to microsurgical system 10 except that it has an irrigation system in addition to the infusion system described above for system 10. More specifically, system 10a is identical to system 10 except that system 10a also includes an irrigation source 200; fluid lines 202 and 206; gas lines 208 and 216; solenoid valves 210 and 218; actuators 214 and 222; electrical interfaces 212 and 220; and a surgical device 224. As shown in FIG. 2, irrigation source 200 is pressurized solely by gravity. As will be appreciated by one of ordinary skill in the art, microsurgical system 10a allows surgical irrigating fluid 140 to be delivered to surgical device 29 via fluid line 80 (infusion), and surgical irrigating fluid 140 to be delivered to surgical device 224 via fluid line 206 (irrigation), independently. Microprocessor 28 can calculate flow information for fluid 140 within fluid line 206 by continuously monitoring the volumetric change of fluid inside chamber 16b, as indicated by fluid sensor 20.

From the above, it may be appreciated that the present invention provides an improved method of controlling intraocular pressure with a microsurgical system. The present invention is illustrated herein by example, and various modifications may be made by a person of ordinary skill in the art. For example, while the present invention is described above relative to controlling intraocular pressure in an ophthalmic microsurgical system, it is also applicable to controlling pressure within the operative tissue during other types of microsurgery.

It is believed that the operation and construction of the present invention will be apparent from the foregoing description. While the apparatus and methods shown or described above have been characterized as being preferred, various changes and modifications may be made therein without departing from the spirit and scope of the invention as defined in the following claims

What is claimed is:

1. A microsurgical system for controlling intraocular pressure, comprising:

a surgical cassette, said surgical cassette having a dual infusion chamber, said dual infusion chamber having a first chamber for holding an irrigating fluid and a second chamber for holding said irrigating fluid, said first chamber not fluidly coupled to said second chamber;
an infusion source external to said surgical cassette and containing said irrigating fluid;
a first fluid level sensor operatively coupled to said first chamber;
a second fluid level sensor operatively coupled to said second chamber;
a pressurized gas source;
a first proportional solenoid valve;
a second proportional solenoid valve;
a first on/off solenoid valve;
a second on/off solenoid valve;
a first pressure transducer;
a second pressure transducer;
a first gas line fluidly coupling said pressurized gas source, said first proportional solenoid valve, said first on/off solenoid valve, said first pressure transducer, and said first chamber in said surgical cassette;
a second gas line fluidly coupling said pressurized gas source, said second proportional solenoid valve, said second on/off solenoid valve, said second pressure transducer, and said second chamber in said surgical cassette;
a surgical device for providing said irrigating fluid to an eye;
a first fluid line fluidly coupling said first chamber in said surgical cassette and said surgical device;
a first actuator operatively coupled with said first fluid line;
a third on/off solenoid valve;
a third gas line fluidly coupling said pressurized gas source, said third on/off solenoid valve, and said first actuator;
a second fluid line fluidly coupling said second chamber in said surgical cassette and said surgical device;
a second actuator operatively coupled with said second fluid line;
a fourth on/off solenoid valve;
a fourth gas line fluidly coupling said pressurized gas source, said fourth on/off solenoid valve, and said second actuator;
a flow sensor operatively coupled to said first fluid line and said second fluid line between said dual infusion chamber in said surgical cassette and said surgical device;
a user input;
a third fluid line fluidly coupling said infusion source and said first chamber in said surgical cassette;
a third actuator operatively coupled with said third fluid line;
a fifth on/off solenoid valve;
a fifth gas line fluidly coupling said pressurized gas source, said fifth on/off solenoid valve, and said third actuator;
a fourth fluid line fluidly coupling said infusion source and said second chamber in said surgical cassette;
a fourth actuator operatively coupled with said fourth fluid line;
a sixth on/off solenoid valve;
a sixth gas line fluidly coupling said pressurized gas source, said sixth on/off solenoid valve, and said fourth actuator; and
a computer electrically coupled to said first proportional solenoid valve, said second proportional solenoid valve, said first fluid level sensor, said second fluid level sensor, said flow sensor, said user input, said first on/off solenoid valve, said second on/off solenoid valve, said third on/off solenoid valve, said fourth on/off solenoid valve, said fifth on/off solenoid valve, and said sixth on/off solenoid valve;
whereby, after priming, said computer opens said first actuator and closes said second actuator so that said first chamber in said surgical cassette is initially active;
whereby when a user selects a desired intraocular pressure via said input, said computer opens said first on/off solenoid valve and sends a first signal to said first proportional solenoid valve to provide an appropriate level of pressurized gas to said first chamber in said surgical cassette so as to provide said irrigating fluid from said first chamber to said surgical device and said eye via said first fluid line, said first pressure transducer senses the pressure within said first gas line, said flow sensor measures a flow rate of said irrigating fluid in said first fluid line and provides a second signal to said computer, said computer calculates a predicted intraocular pressure using said second signal and empirically determined impedance information for said microsurgical system, and said computer sends a third signal to said first proportional valve to maintain said predicted intraocular pressure proximate said desired intraocular pressure;
whereby when said first fluid level sensor determines that a level of said irrigating fluid in said first chamber in said surgical cassette has reached a bottom limit level, said computer closes said first actuator and opens said second actuator so that said second chamber in said surgical cassette is active and provides said irrigating fluid in said second chamber to said surgical device and said eye via said second fluid line, and said computer also opens said third actuator so that said first chamber in said surgical cassette is refilled with said irrigating fluid from said infusion source via said third fluid line;
whereby said computer closes said first on/off solenoid valve, opens said second on/off solenoid valve, and sends a fourth signal to said second proportional solenoid valve to provide an appropriate level of pressurized gas to said second chamber in said surgical cassette so as to provide said irrigating fluid from said second chamber to said surgical device and said eye via said second fluid line, said second pressure transducer senses the pressure within said second gas line, said flow sensor measures a flow rate of said irrigating fluid in said second fluid line and provides a fifth signal to said computer, said computer calculates a predicted intraocular pressure using said fifth signal and empirically determined impedance information for said microsurgical system, and said computer sends a sixth signal to said second proportional solenoid valve to maintain said predicted intraocular pressure proximate said desired intraocular pressure; and
whereby when said second fluid level sensor determines that a level of said irrigating fluid in said second chamber in said surgical cassette has reached a bottom limit level, said computer closes said second actuator and opens first second actuator so that said first chamber in said surgical cassette is again active and provides said irrigating fluid in said first chamber to said surgical device and said eye via said first fluid line, and said computer also opens said fourth actuator so that said second chamber in said surgical cassette is refilled with said irrigating fluid from said infusion source via said fourth fluid line.

* * * * *